United States Patent [19]

Odén et al.

[11] Patent Number: 5,106,303
[45] Date of Patent: Apr. 21, 1992

[54] METHODS OF MAKING ARTIFICIAL TOOTH ONLAYS AND INLAYS

[75] Inventors: Agneta E. Odén, Stocksund; Knut M. G. Andersson, Lerum, both of Sweden

[73] Assignee: Sandvik AB, Sandviken, Sweden

[21] Appl. No.: 497,620

[22] Filed: Mar. 23, 1990

[30] Foreign Application Priority Data

Mar. 23, 1989 [SE] Sweden .................. 8901049

[51] Int. Cl.$^5$ .................................... A61C 5/10
[52] U.S. Cl. ........................ 433/223; 433/218; 433/226; 433/228.1
[58] Field of Search .............. 433/223, 226, 228.1, 433/222.1, 218

[56] References Cited

U.S. PATENT DOCUMENTS

| | | | |
|---|---|---|---|
| 3,541,688 | 11/1970 | McLean et al. | 433/222.1 |
| 3,861,044 | 1/1975 | Swinson, Jr. | 433/226 |
| 4,585,417 | 4/1986 | Sozio et al. | 433/222.1 |
| 4,789,649 | 12/1988 | Abert et al. | 433/202.1 |
| 4,793,809 | 12/1988 | Sigler et al. | 433/222.1 |
| 4,937,928 | 7/1990 | van der Zel | 433/223 |

*Primary Examiner*—John J. Wilson
*Attorney, Agent, or Firm*—Burns, Doane, Swecker & Mathis

[57] ABSTRACT

The present invention relates to artificial onlay tooth crowns or inlays composed of a prefabricated core designed for preparations for onlay tooth crowns or inlays in natural teeth. The core is preferably fabricated from a high strength densely sintered ceramic material by copy milling from a negative reproduction from the prepared cavity to a compacted body or a presintered ceramic material. During the copy milling, the sintering shrinkage is considered by enlargement of the copy milled compacted body or the presintered body corresponding to the sintering shrinkage. The onlay tooth crown and inlays are given the final shape by shaping the surfaces outside the cavity of the compacted or the presintered body. After the final sintering, the external surface can be shaped and a veneer material attached to the external surface of the core by, e.g., firing of dental porcelain. The manufacture of onlay tooth crowns or an inlay according to the method of the invention decreases essentially the manufacturing time for onlay tooth crowns and inlays and at the same time the strength and the accuracy to shape increase.

6 Claims, 2 Drawing Sheets

METHODS OF MAKING ARTIFICIAL TOOTH ONLAYS AND INLAYS

BACKGROUND OF THE INVENTION

This invention relates to accurately shaped artificial, all ceramic onlay tooth crowns and inlays as replacement for lost tooth structure. By starting from a negative reproduction of the prepared tooth and then copy milling a surface which will fit into the prepared cavity, a tooth crown or an inlay is obtained which is easier to produce and of lower cost. In addition, the onlay crown or inlay has higher strength and a more accurate shape. Preferably the coping is manufactured from a biocompatible, high strength ceramic material, which is sintered to high density.

Artificial tooth crowns and inlays made from a metal are today manufactured mainly in the following way: A dentist makes a preparation on a tooth, on which a dental construction is to be fixed in the mouth of a patient, an impression is made and with this impression a copy of the preparation is made in gypsum. On this model, a dental technician prepares a crown in wax. The adjacent teeth must be considered, and the dental technician must have models from the two jaws. A sprue former of wax is fixed on one of the cusps of the wax crown. The wax crown is loosened from the gypsum model. The wax crown with the sprue former are invested in a metal ring with investment. The wax is burnt out and a crown can be cast in a precious or non-precious metal. The cast crown can, in certain cases, be covered by a veneer made of porcelain in order to obtain a color of the tooth crown similar to the color of natural teeth. Instead of porcelain, plastic material can be used.

The fabrication of tooth crowns in glass is very close to the technique described above with the difference that after the casting, a thin layer of porcelain is painted on the surface and fired in order to give the tooth crown individual tooth colors.

Tooth crowns fabricated mainly of porcelain can be made with conventional dental porcelain technique from a sheet made of a precious alloy. Porcelain crowns and inlays can also be made with conventional dental porcelain technique on a model of the abutment. The material of this model does not change dimensions on heating up to 1200° C. When the tooth crown or the inlay is ready, the model of the abutment is removed by sand blasting.

The above described complicated and time consuming methods are used to manufacture crowns and inlays, which will fit in individually prepared cavities in natural teeth.

The problem with the material now used (porcelain, glass, etc.) in artificial tooth crowns is their brittleness, which often gives early fracture, and these artificial crowns and inlays must be replaced more or less regularly.

OBJECTS AND SUMMARY OF THE INVENTION

One object of the present invention is to provide artificial tooth crowns and inlays, which are easier and accordingly cheaper to make and, in addition, have higher strength and more accurate shape and a method of making such tooth crowns and inlays.

Another object is to make an inlay or an onlay tooth crown by using densely sintered, high strength ceramic material, provided that the demand of high strength, accuracy to shape (which includes compensation for any shrinkage during sintering) can be combined with the demands on the application of porcelain concerning burning, adherence, biocompatibility and esthetics.

In accordance with one aspect of the present invention there is provided an artificial onlay tooth crown or inlay for fit into a prepared tooth cavity comprising a core and a veneer overlying at least part of the core which does not fit into the said cavity, the boundary surface of the core which fits into said cavity being formed by copy milling a negative reproduction of the said cavity.

In accordance with another aspect of the present invention there is provide a method of making an artificial onlay tooth crown or inlay for fit into a prepared tooth cavity comprising: forming a negative reproduction of said cavity; copy milling a core from said negative reproduction including a surface abutting said cavity and an external surface; and applying a veneer to at least part of the said external surface of said core.

In accordance with a further aspect of the present invention there is provided a method of filling a tooth cavity with an artificial onlay tooth crown or inlay which comprises forming an artificial onlay tooth crown or inlay by the method of the preceding paragraph and adhesively fitting said onlay tooth crown or inlay into said tooth cavity.

DETAILED DESCRIPTION OF THE PREFERRED EMBODIMENTS

Figure 1:
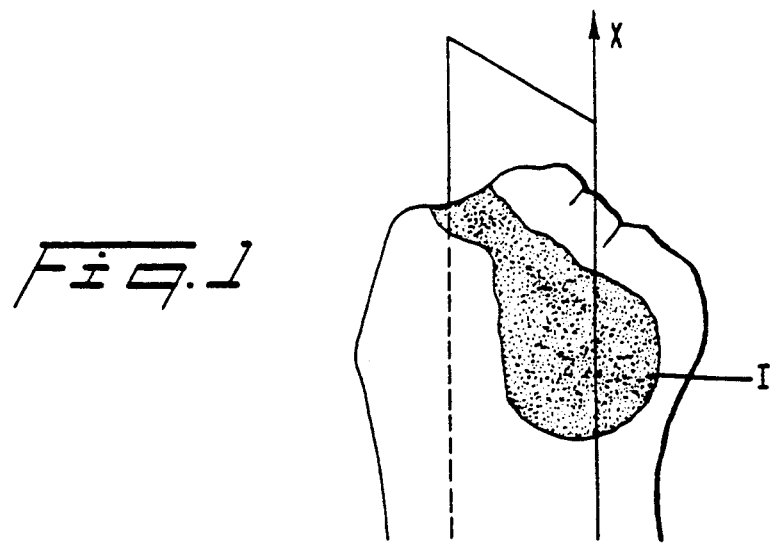
FIG. 1 is a schematic representation of a natural tooth with an artificial inlay (dotted).

FIG. 1 shows an artificial inlay (shown as the dotted portion) in a natural tooth. In the Figure, the border between the cavity E and the inlay core B is indicated as I, the axis of the tooth as X.

Figure 2:
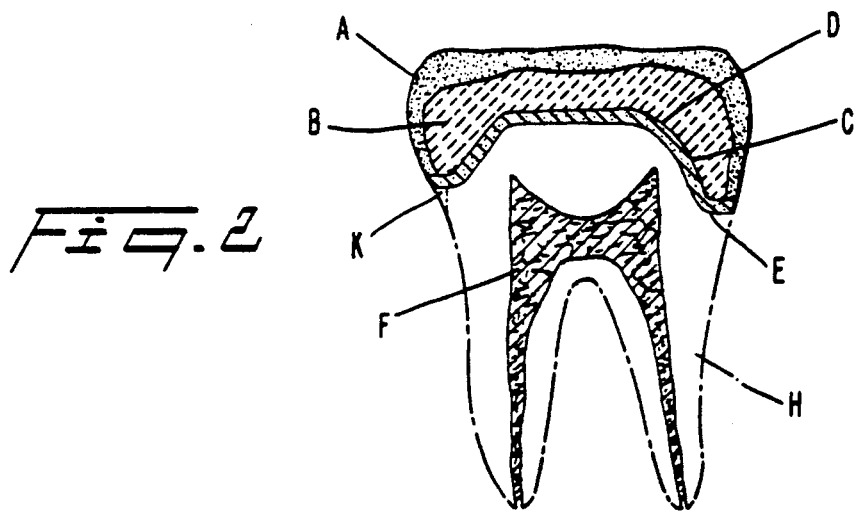
FIG. 2 is a representation of a cross section of a natural tooth with an inlay.

FIG. 2 shows a cross section of an inlay in a natural tooth. In this Figure, the veneer is indicated as A, the core made from dense sintered ceramic as B, the cement as C, the copy milled surface of the core as D, the prepared surface of cavity as E, the pulp as F, and the natural tooth root as H.

Figure 3:
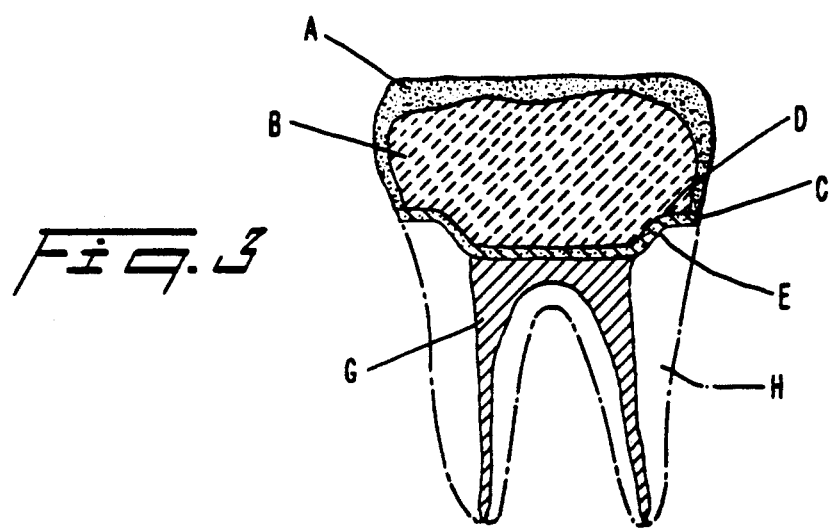
FIG. 3 is a representation of a cross section of a root-filled natural tooth with an inlay.

FIG. 3 shows a cross section of an alternative design for a root-filled tooth, the same letters meaning the same things as in FIG. 2, while a root filling is indicated as G.

Figure 4:
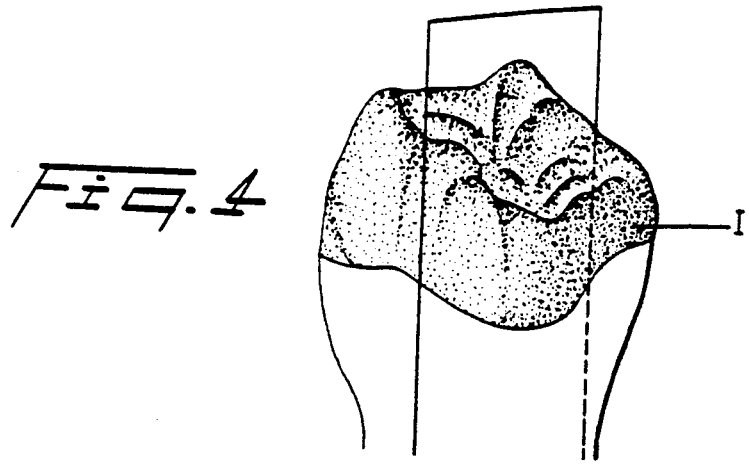
FIG. 4 is a schematic representation of a natural tooth with an onlay tooth crown (dotted).
Figure 5:
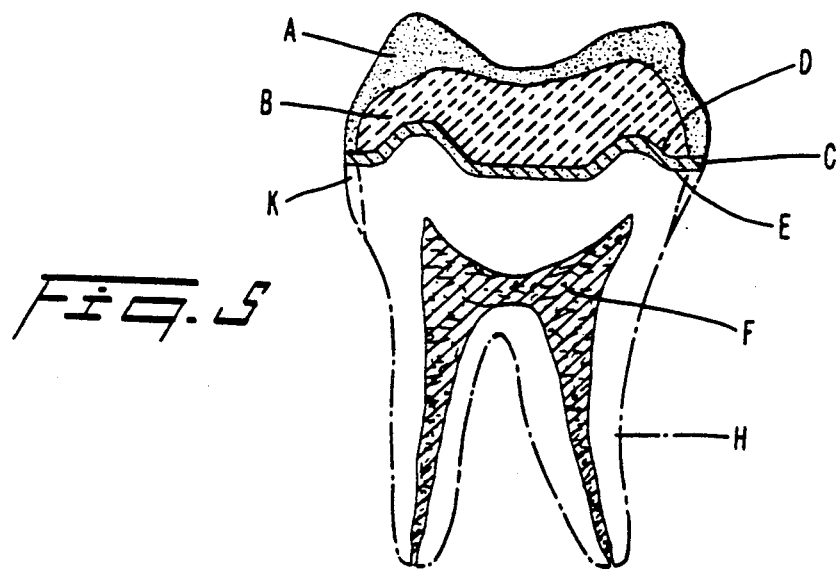
FIG. 5 is a representation of a cross section of a natural tooth with an onlay tooth crown.
Figure 6:
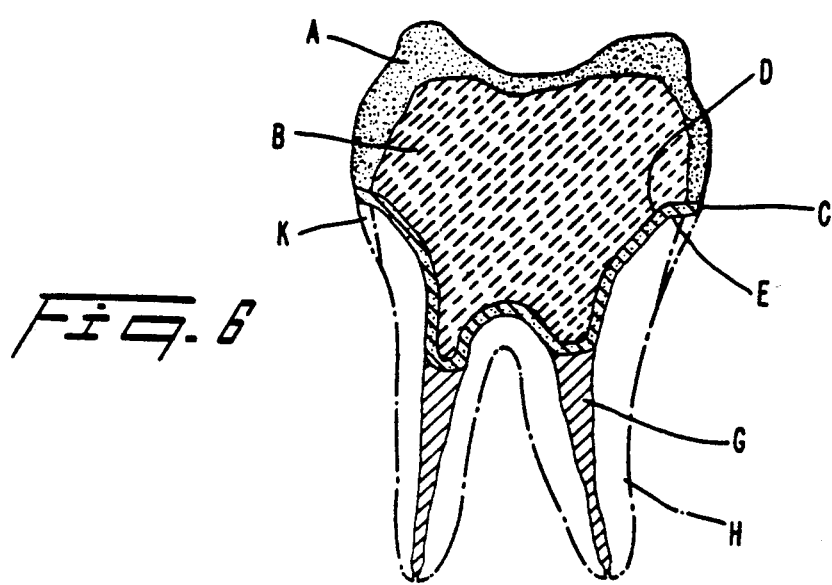
FIG. 6 is a representation of a cross section of a root-filled tooth with an onlay tooth crown.

FIG. 4 shows an artificial onlay in a natural tooth, the onlay being the dotted portion while FIG. 5 shows a cross section of an onlay tooth crown on a natural tooth, and FIG. 6 shows a cross section of an alternative design for an onlay tooth crown for a root-filled tooth, the same letters meaning the same things as with FIGS. 1, 2 and 3.

In each of the Figures, the artificial onlay tooth crown or the inlay are the combination of the core B with the veneer A. They are fixed in the prepared cavity E with cement C.

According to the present invention, artificial onlay tooth crowns and inlays are made in which the core is prefabricated from a biocompatible material with the part D of the outer surface of the core given such dimensions as to fit into a prepared cavity E, which can be a preparation for an inlay or a preparation for an onlay tooth crown or a preparation for a tooth crown on a root canal pin. A biocompatible material for the core is a material which is not toxic and does not cause damage to oral tissues or does not give unwanted system effects. In addition this material must not discolor or otherwise give unwanted effects to the veneer material. The onlay tooth crowns and the inlays are fixed by cementation in the cavities.

The present invention considerably simplifies the handicraft of the dental technician. With the aid of gypsum models of the two jaws and with the prefabricated core placed on the model of the tooth preparation, a dental technician can make the final design of the onlay tooth crown or inlay and at the same time control their function and size. In order to make the veneer, a porcelain furnace or an apparatus for pressing of composite veneer is needed. The method of making a tooth crown or an inlay to fit into an existing preparation according to the present invention essentially decreases the production time for these constructions and at the same time increases its strength and accuracy of shape.

Cores according to the invention can be made from metals or alloys (e.g., titanium or dental alloys), plastic, porcelain, glass-ceramic or apatite-ceramic by copy milling a negative reproduction of the prepared cavities (E). Copy milling accurately matches the boundary surface D of the onlay tooth crown or of the inlay to the cavity E. A negative reproduction is made by making an impression of the prepared tooth or a model from this tooth together with its adjacent teeth. The impression material fills up the whole cavity and when the impression is removed from the teeth, this impression comprises the surface D and the contact points to the adjacent teeth. From the impression, material closest to surface D is adjusted in order to have this surface D within reach for copy milling. The contacts with the adjacent teeth give the limitation in mesial distal direction. The contour outside the cavity is prepared manually with conventional dental technical machining practice. A negative reproduction can be, e.g., a Kerr impression or a silicon impression.

Preferably, the core according to the invention is made from a biocompatible densely sintered, high strength ceramic material. On the obtained core, the veneer is built up, so that the final product will be a tooth crown or an inlay fitting into an existing preparation and to the actual whole set of teeth.

As can be seen from FIG. 2 and FIG. 3, artificial inlays are made as a core of densely sintered ceramic B with veneer A. They are fixed in the prepared cavity E by, e.g., cementing. The thin layer of cement C connects the prepared cavity walls E with that part of the surface D of the inlay or the onlay tooth crown, which has been made so that this surface D fits with great precision into the prepared cavity E. The layer of cement can have a thickness <200 μm, preferably 25-75 μm. Artificial onlay tooth crowns are made as a core of densely sintered ceramic B with veneer A. As can be seen from FIG. 6, the preparation of a root filled tooth can be extended down into the root canals in order to have optimum retention of the tooth crown. The veneer A can be made from dental porcelain or plastic. The cementing of the constructions can be made with conventional adhesives with, e.g., glassionomercement, phosphatecement, or a resin. In the latter case, it can be an advantage to silane treat the surfaces D of the constructions which will be joined with the prepared surfaces of the tooth structure. The enamel walls of the prepared cavity can be etched and the dentin walls of the prepared cavity E can be treated with dentine adhesive before the above described restorations are cemented with resin, which resin can contain filler particles of, e.g., ceramic or polymer material. The preparation of the cavity is made without an undercut. Undercuts can be blocked with some cement, e.g., glassionomercement.

The ceramic powder can be made by several well known methods. Traditional powder metallurgical techniques can be used, where the different components are mixed and ground under dry or wet conditions with water or an inorganic solvent (e.g., alcohols) as grinding liquid. The so-called SOL-GEL technique can also be used where different oxide materials are deposited together from a water solution or are co-precipitated from metal alcoxides in e.g., water-free alcohol by controlled addition of water. A combination of different techniques can also be used by using SOL-GEL technique to deposit a surface layer of desired metal oxide on a powder material. Lubricants or other organic binders depending on the choice of forming method may be added to the ceramic powder when needed at suitable times in the process as is conventionally known. Other preparation routes of the ceramic material are also possible such as reaction sintering where a suitable metal is oxidized, nitrided, etc. For example, aluminum can be oxidized under carefully controlled processing to alumina. These methods allow preforming or reinforcement by fibers, e.g., in a felt infiltrated with liquid metal.

Many of the monolithic ceramics which are biocompatible may have a brittle performance if they are not sintered to nearly full density, more than 98% and preferably >99.5% of the theoretical density. However, these ceramics can be strengthened by a number of toughening mechanisms. Finely dispersed particles, platelets, whiskers or fibers raise the fracture toughness of the composite. Typical additives are the nitrides, carbides, borides or mixtures thereof of the transition metal of group IV—VI or the elements Al or Si. Toughening may also be achieved by so-called transformation toughening, i.e., additions of unstabilized $ZrO_2$ or $ZrO_2$ stabilized with $Y_2O_3$, MgO or CaO. The additions of these latter oxides shall not exceed 25 wt %, but should be more than 2 wt %. The best performance is obtained with 3-12 wt % of the $ZrO_2$.

The powder with lubricants and/or other organic binders is cold isostatically compacted, uniaxially pressed, slip cast, pressure cast, injection moulded or compacted in another suitable way. The compacted body has such dimensions that it comprises enough material for the copy milling of the outer shape of the core, which will fit into the prepared cavity E. During this copy milling, the sintering shrinkage must be considered. Thus, the copy milled surface D must be enlarged so that the compacted body has such dimensions that after the shrinkage during the subsequent sintering process to high density, it has the desired final geometrical external shape D which will fit into the prepared cavity E with great accuracy.

The ceramic body can also be presintered before the copy milling of the surface D fitting to the prepared cavity E. All the other surfaces are prepared to near final shape before the final sintering. It is important that the ceramic material is sintered to closed porosity, which for an oxide material means at least 95% of theoretical density, but in order to ensure good mechanical strength the material should preferably have a density over 98%, while densities over 99.5% give the best strength.

The sintering can take place in a vacuum or under hydrogen atmosphere, under normal atmospheric pressure or under increased pressure in connection with the overpressure sintering or hot isostatic compaction or alternatively by hot pressing. Highly pure $Al_2O_3$ become translucent during sintering to full density in vacuum or in hydrogen atmosphere, which is an advantage when natural teeth are to be imitated. Pure oxide material can be sintered in air, but some composites have to be sintered in inert or controlled atmosphere. The core is given an external shape so that the building-up of the veneer is facilitated. The external shape can be such that it is roughly similar to natural teeth. After the final sintering, the surfaces of the core may need some grinding, especially the external surfaces outside the prepared cavity. This grinding will be made with the inlay or the onlay crown on a model of the prepared tooth. If dental porcelain is used as the veneer with a coefficient of thermal expansion adapted to the material of the core, the porcelain will adhere better. In the case of $Al_2O_3$ as the core material there will be a "chemical bond" between $Al_2O_3$ and porcelain. This means that the external surface of the core does not need any retention elements. When using other veneer materials, e.g., plastic, mechanical retention elements can be needed, e.g., grooves, pits or on the external surface sintered retention elements or a silane treatment of the surface. The core can also be given such a shape that the ceramic inlay or onlay tooth crown does not need any veneer material. The surfaces of the inlay or the onlay tooth crown which is a part of the external surfaces of the repaired tooth must in this case before the cementing be ground and polished to a surface fineness of 0.5-5 $\mu m$, preferably 0.5-1 $\mu m$.

The ceramic base material in the core comprises preferably one or several biocompatible oxides (including phosphates, silicates and sulfates), with the additives of carbides, silicides, nitrides or borides with or without binder metal (preferably iron-group metals) in addition to conventional sintering aids. The base material can also comprise other biocompatible high performance ceramics such as nitrides, oxynitrides, cabides, etc. Examples of the two former materials are $Si_3N_4$, $Si_2N_2O$, sialon, AlN, AlON, etc. Examples of biocompatible oxides, which can form base matrix for the ceramic body, are $Al_2O_3$, $TiO_2$, MgO, $ZrO_2$ (partly or totally stabilized with amounts of up to 25 weight % of $Y_2O_3$, MgO or CaO).

Also, components such as SiC, TiN, TiC, $TiB_2$, $Si_3N_4$, or other biocompatible carbides or nitrides of group IV, V or Vi can be present as particles with a size of <25 $\mu m$, preferably <10 $\mu m$, and/or as whiskers (hair shaped single crystals) with a length to diameter ratio >5, preferably >10, and/or fibers (polycrystalline) with a diameter >10 $\mu m$ and/or as single crystal platelets with an approximate diameter of 5-50 $\mu m$, preferably 50 $\mu m$, and a thickness of 1-10 $\mu m$, preferably 1-4 $\mu m$. The amount of whiskers, fibers and/or platelets should not exceed 60 volume preferably less than 40 volume %.

In a preferred embodiment, the ceramic material comprises >50%, preferably >85%, by weight of $Al_2O_3$ with additives of conventional sintering aids. In order to increase the strength <25 weight %, preferably 3-12 weight %, of $ZrO_2$, and/or 5-40 weight %, preferably 10-30 weight %, of SiC whiskers can be added. In order to get a suitable color, colored components can be chosen. Additives, e.g., 0.1-10 weight %, preferably 0.5-5, weight %, of TiN and/or ZrN will give $Al_2O_3$ based inlays and onlay crowns a faint yellow shade.

The invention is additionally illustrated in connection with the following Example which is to be considered as illustrative of the present invention. It should be understood, however that the invention is not limited to the specific details of the Example.

EXAMPLE

A core to fit a prepared cavity in a molar according to FIG. 5 was made from a powder with the approximate composition 99.85 weight % of $Al_2O_3$ and 0.15 weight % MgO. Blocks (15 mm × 15 mm × 30 mm) of the powder were uniaxially compacted and presintered at 1200° C. An impression was made of the tooth with the prepared cavity with a puttymass of a silicon impression material. This impression contained the negative reproduction D of the prepared cavity walls E. With a scalpel, the impression material outside the boundary I was carefully removed. From the impression with use of the presintered blocks the surface D was copy milled and at the same time enlarged to such a size that it allowed a shrinkage of 16.5% during the sintering. From the boundary I the external surface of the core was milled and machined to a minimum thickness of the core of 1.2 mm in the direction of the axes through the tooth. The sintering was performed in air during 2 hours at 1600° C. After the sintering the core had a relative density of 99.5% and a minimum thickness of 1 mm in the direction of the axes through the tooth. An ordinary impression was made from the whole jaw and from this impression a model of the jaw was made in gypsum. The core fitted perfectly into the prepared cavity and commercially available dental porcelain was fired on the surface. The first layer porcelain comprised about 50% $Al_2O_3$ and was fired at 1150° C. during 10 minutes. During the heating the furnace was under vacuum, but when the final firing temperature was reached the firing was performed under atmospheric pressure. The remainder of the crown was fired at 960° C. The dental porcelain combined chemically with the alumina without any gap between the porcelain and the densely sintered core. The onlay crown fitted perfectly on the model of the tooth and was ready to be cemented with conventional methods in the tooth cavity in the mouth of a patient.

The principles, preferred embodiments and modes of operation of the present invention have been described in the foregoing specification. The invention which is intended to be protected herein, however, is not to be constructed as limited to the particular forms disclosed, since there are to be regarded as illustrative rather than restrictive. Variations and changes may be made by those skilled in the art without departing from the spirit of the invention.

We claim:

1. A method of making an artificial onlay tooth crown or inlay for fit into a prepared tooth cavity comprising: forming a negative reproduction of said cavity; copy milling a core from said negative reproduction including a surface abutting said cavity and an external surface; and applying a veneer to at least part of the said external surface of said core.

2. The method of claim 1 wherein said core which is copy milled is a presintered body which is thereafter sintered.

3. A method of making an artificial onlay tooth crown or inlay according to claim 2 wherein the ceramic material of the core comprises at least one of the oxides $Al_2O_3$, $TiO_2$, MgO, $ZrO_2$ and $ZrO_2$ with up to 25 mole % of at least one of $Y_2O_3$, MgO and CaO.

4. The method of claim 1 wherein said core comprises a biocompatible ceramic material with a relative density >95%.

5. A method of making an artificial onlay tooth crown or inlay according to claim 4 wherein the ceramic material of the core comprises at least one of the oxides $Al_2O_3$, $TiO_2$, MgO, $ZrO_2$ or $ZrO_2$ with up to 25 mole % of at least one of $Y_2O_3$, MgO and CaO.

6. A method of filling a tooth cavity with an artificial onlay tooth crown or inlay forming an artificial onlay tooth crown or inlay comprising forming a negative reproduction of said cavity; copy milling a core from said negative reproduction including a surface abutting said cavity and an external surface; applying a veneer to at least part of the said external surface of said core; and adhesively fitting said onlay tooth crown or inlay into said tooth cavity.

* * * * *